(12) United States Patent
Ewonce et al.

(10) Patent No.: US 6,725,864 B2
(45) Date of Patent: Apr. 27, 2004

(54) SURGICAL SHOULDER DRAPE WITH POUCH

(75) Inventors: John E. Ewonce, Gurnee, IL (US); Rogelio Reyes, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 49 days.

(21) Appl. No.: 10/097,160

(22) Filed: Mar. 13, 2002

(65) Prior Publication Data

US 2002/0174870 A1 Nov. 28, 2002

Related U.S. Application Data

(60) Provisional application No. 60/276,021, filed on Mar. 15, 2001.

(51) Int. Cl.[7] ............................................. A61B 19/00
(52) U.S. Cl. ....................................... 128/849; 128/853
(58) Field of Search ................................. 128/849–856

(56) References Cited

U.S. PATENT DOCUMENTS

| | | | |
|---|---|---|---|
| 4,974,604 A | 12/1990 | Morris | 128/853 |
| 5,002,069 A | 3/1991 | Thompson et al. | 128/849 |
| 5,143,091 A | 9/1992 | Patnode et al. | 128/853 |
| 5,383,476 A | 1/1995 | Peimer et al. | 128/849 |
| 5,494,050 A | 2/1996 | Reyes | 128/849 |
| 5,513,655 A | 5/1996 | Peimer et al. | 128/849 |
| 5,618,278 A | 4/1997 | Rothrum | 604/356 |
| 5,871,014 A | 2/1999 | Clay et al. | 128/849 |
| 6,032,670 A | 3/2000 | Miller | 128/849 |

*Primary Examiner*—Michael A. Brown
(74) *Attorney, Agent, or Firm*—Andrew G. Rozycki (57) ABSTRACT

The invention disclosed herein provides for a surgical drape having a shoulder pouch useful for arthroscopic surgery. The shoulder pouch comprises a single folded sheet of flexible fluid impervious material with an opening in the rear central portion covered by an elastomeric sheet. The elastomeric sheet contains a contoured opening adapted to the anatomy of the shoulder. The top front portion of the pouch contains a wire running along the top edge and exiting at the rear portion, and a conformable strip located at the upper front portion as well. The shoulder pouch of the invention is anatomy specific and affords the practitioner increased control over the configuration of the drape and pouch throughout a surgical procedure.

5 Claims, 9 Drawing Sheets

SURGICAL SHOULDER DRAPE WITH POUCH

RELATED APPLICATION DATA

This application is based on provisional patent application Serial No. 60/276,021 filed Mar. 15, 2001.

FIELD OF THE INVENTION

The invention relates to the field of surgical equipment. In particular, the invention pertains to arthroscopic surgical drapes having pouches which collect and contain fluids.

BACKGROUND OF THE INVENTION

During surgical procedures, it is often desirable to create a sterile field surrounding the surgical site in order to reduce the likelihood of infection in the patient. Sterile materials such as surgical drapes have been used to create such a sterile field while allowing openings to be created or formed in the material to permit access by the surgeon to the surgical site. Surgical drapes function to prevent bacterial and viral contamination of the practitioner by the patient, as well as contamination of the patient by the staff and environment during surgery.

Some surgical procedures including many arthroscopic techniques generate a large volume of fluid as a result of exiting body fluids or irrigation of the surgical site. Thus, the collection, containment and disposal of such fluids is often necessary during the procedure. Fluid collection pouches are often used during such procedures for this purpose.

Arthroscopic and orthopedic surgeries typically involve anatomy-specific procedures. Often the surgical instruments and equipment used in these procedures are adapted for the particular anatomy of the surgical site. Anatomy specific fluid collection pouches and drape assemblies are known. For example, Reyes U.S. Pat. No. 5,494,050 discloses an arthroscopy pouch specifically adapted for use in knee surgery. An arthroscopy pouch and drape assembly adapted for use with the knee, however, would not necessarily contain structural features suitable for use with other parts of the body.

There exists a need in the surgical field for improved surgical pouches and drape assemblies having features thereon which accommodate the patient's natural anatomical geometry at the shoulder while preserving the sterility requirements and enhance the practitioner's performance of the procedure.

SUMMARY OF THE INVENTION

The invention is an improved shoulder drape comprising a pouch which can be used in arthroscopic surgery. The shoulder drape contains a combination of advantageous structural features uniquely adapted to accommodate the anatomy of the shoulder and surrounding area while at the same time permits the desired surgical access to the site during arthroscopic surgery. The shoulder drape and pouch assembly of the invention comprises a conformable strip positioned within the front portion of the pouch to enhance conformability to the pouch in addition to the wire drawstring. The pouch portion is affixed to a drape likewise having a single opening, thereby eliminating the need to further cut or create seams in the drape portion, or otherwise structurally modify the shoulder drape. Furthermore, the shoulder drape of the invention is adapted for use with either the left or right shoulder without the need for structural modifications. The shoulder drape is constructed such that in use, the drape covers the remaining part of the patient's body and equipment, and effectively forms an anesthesia screen.

The invention provides for a surgical shoulder pouch for use with a drape, said pouch comprising:
 a) a single folded sheet of flexible fluid impermeable material having a front distal portion and a rear proximal portion relative to the patient's body, and top portion and bottom portion;
 b) a central region located on said rear portion of the flexible sheet having an opening;
 c) an elastomeric sheet covering said opening in the flexible sheet, the elastomeric sheet having a contoured opening therethrough smaller in size than the opening in the flexible sheet, the perimeter portion of said elastomeric sheet being fixed to the perimeter portion of the opening of the flexible sheet so that the flexible sheet circumscribes the perimeter of the elastomeric sheet;
 d) a longitudinal wire having a middle portion inside of a seam running along the upper edge of the top portion of the front portion of the pouch, and having ends exiting the front portion of the pouch proximal to the rear portion of the pouch; and
 e) a conformable strip positioned at the central region of the front portion of the pouch adjacent the upper edge.

The elastomeric sheet and contoured opening therethrough are adapted to accommodate the natural geometry of the patient's anatomy at the shoulder region and to create a seal surrounding the shoulder when the patient's arm is inserted through the opening. In a preferred embodiment of the invention, the opening in the elastomeric sheet is pear-shaped to accommodate the natural anatomy of the shoulder. The longitudinal wire and conformable strip each function cooperatively to permit adjusting of the configuration of the front upper edge of the pouch and maintain such configuration during the surgical procedure.

The invention also provides for a surgical shoulder drape comprising a pouch, said pouch comprising:
 a) a single folded sheet of flexible fluid impermeable material having a front distal portion and a rear proximal portion relative to the patient's body, and top portion and bottom portion;
 b) central region located on said rear portion of the flexible sheet having an opening;
 c) an elastomeric sheet covering said opening in the flexible sheet, the elastomeric sheet having a contoured opening therethrough smaller in size than the opening in the flexible sheet, the perimeter portion of said elastomeric sheet being fixed to the perimeter portion of the opening of the flexible sheet so that the flexible sheet circumscribes the perimeter of the elastomeric sheet;
 d) a longitudinal wire having a middle portion inside of a seam running along the upper edge of the top portion of the front portion of the pouch, and having ends exiting the front portion of the pouch proximal to the rear portion of the pouch; and
 e) a conformable strip positioned at the central region of the front portion of the pouch adjacent the upper edge;
 wherein the exterior of the rear portion of said pouch is affixed to a surgical drape having an opening in alignment with said opening in the elastomeric sheet of the pouch.

In a preferred embodiment, the drape portion comprises a patient-contacting surface comprising at least one adhesive portion adapted to adhere the drape onto the patient's body.

DETAILED DESCRIPTION OF THE INVENTION

The term "pear-shaped" and inflections thereof as used herein is meant to describe the shape of the contoured opening through the elastomeric sheet. The narrower end of the opening is generally located at the lower portion of the opening relative to the intended positioning upon the patient, i.e., near the armpit. Thus, the widest end of the opening is generally located at the upper portion of the opening such that when placed upon the patient, the widest portion resides on top of the patient's shoulder.

Figure 1:
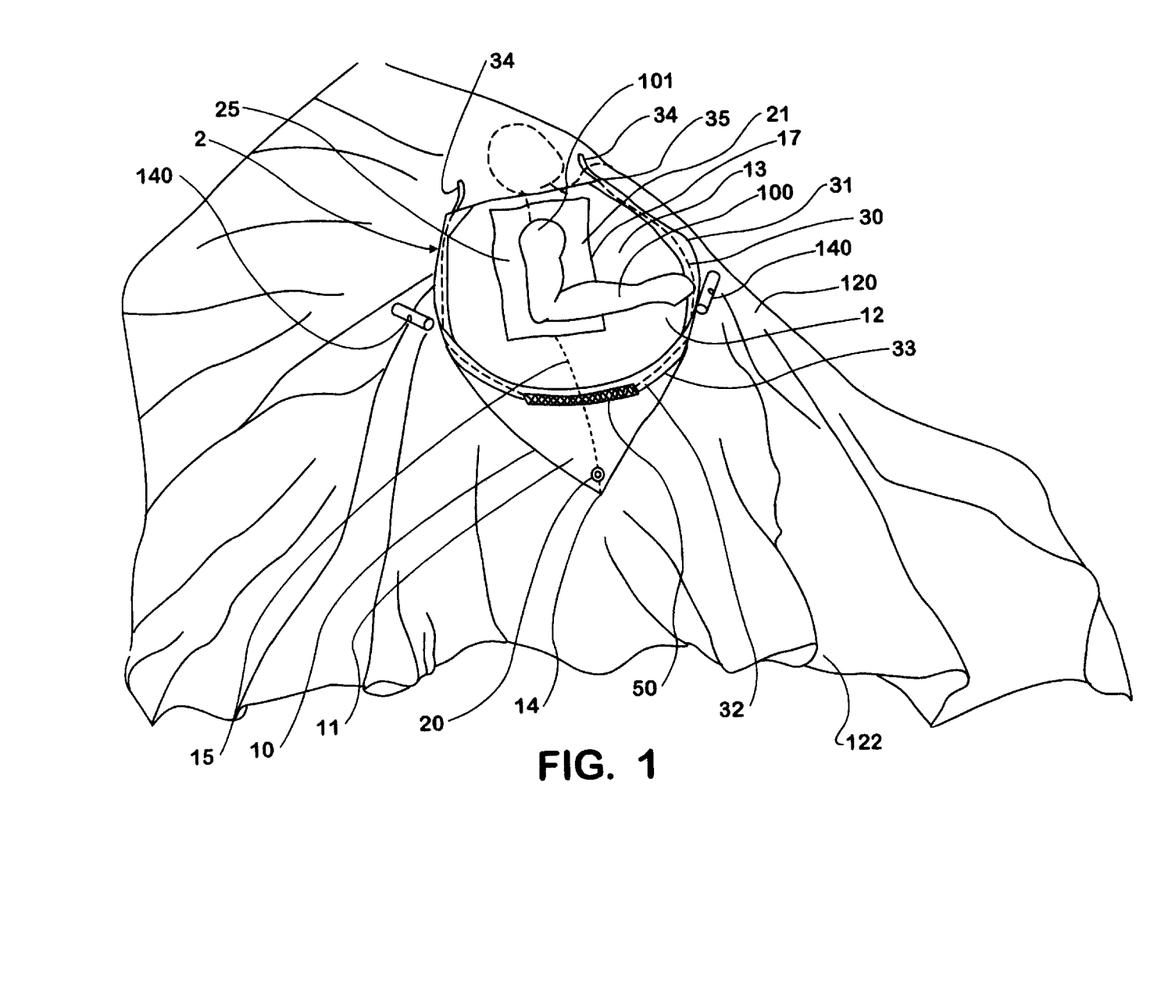
FIG. 1 is a perspective view of the shoulder drape and pouch positioned on a patient in accordance with one embodiment of the invention.
Figure 2:
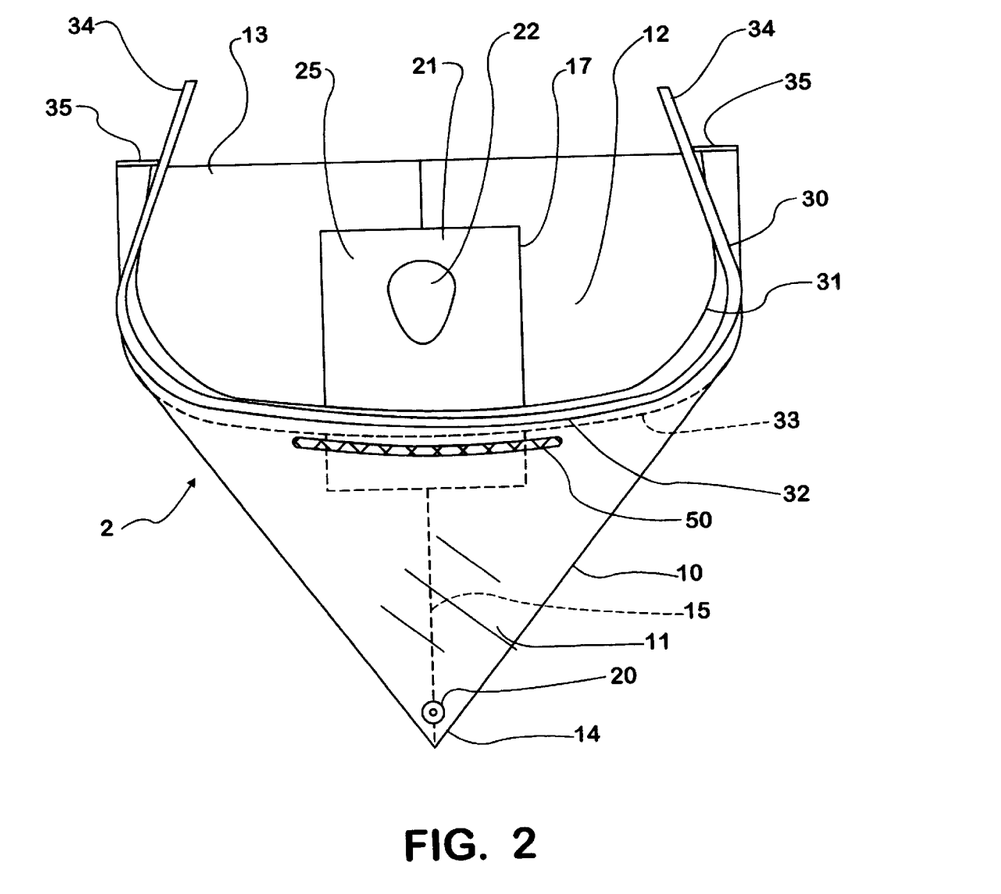
FIG. 2 is a front view of the shoulder pouch in an open position according to one embodiment of the invention.
Figure 3:
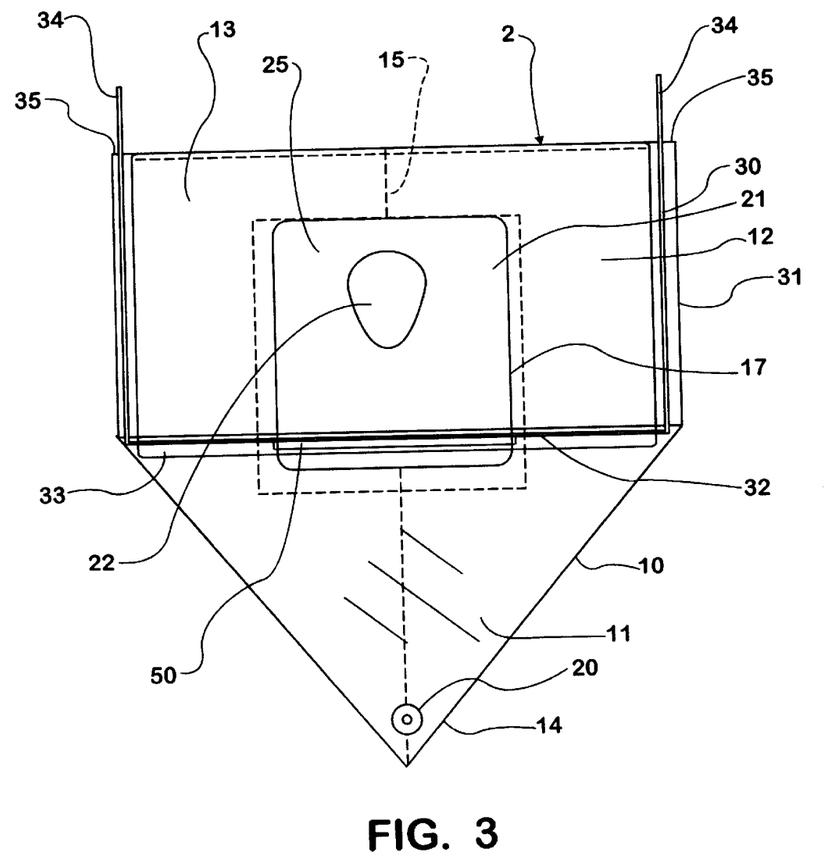
FIG. 3 is a front view of the shoulder pouch in a flattened position according to one embodiment of the invention.
Figure 4:
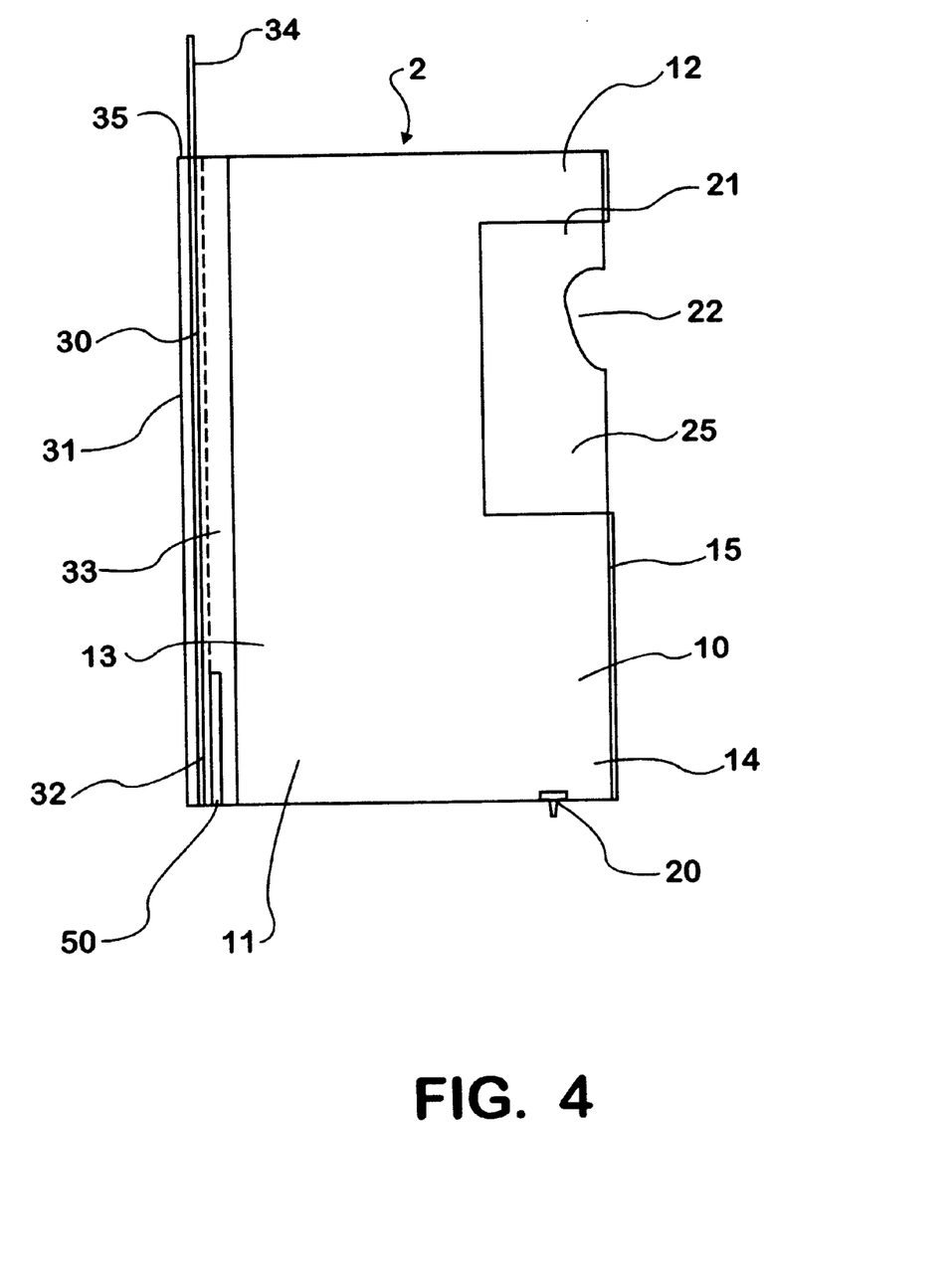
FIG. 4 is an exterior view of the shoulder pouch in folded position as folded along a central vertical line in accordance with one embodiment of the invention.
Figure 5:
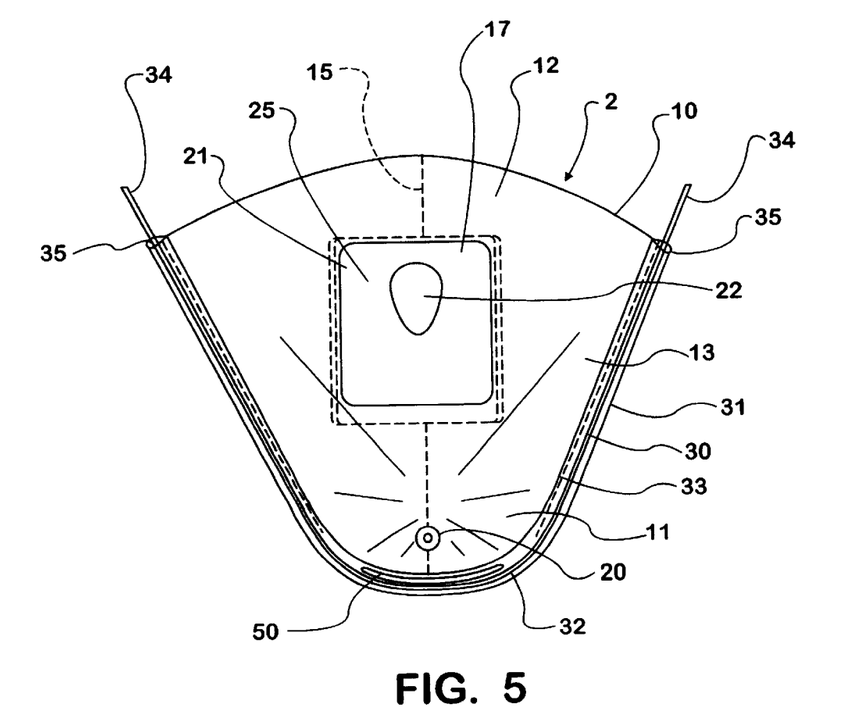
FIG. 5 is a top view of the shoulder pouch in open position showing the interior of the device according to one embodiment of the invention.
Figure 6:
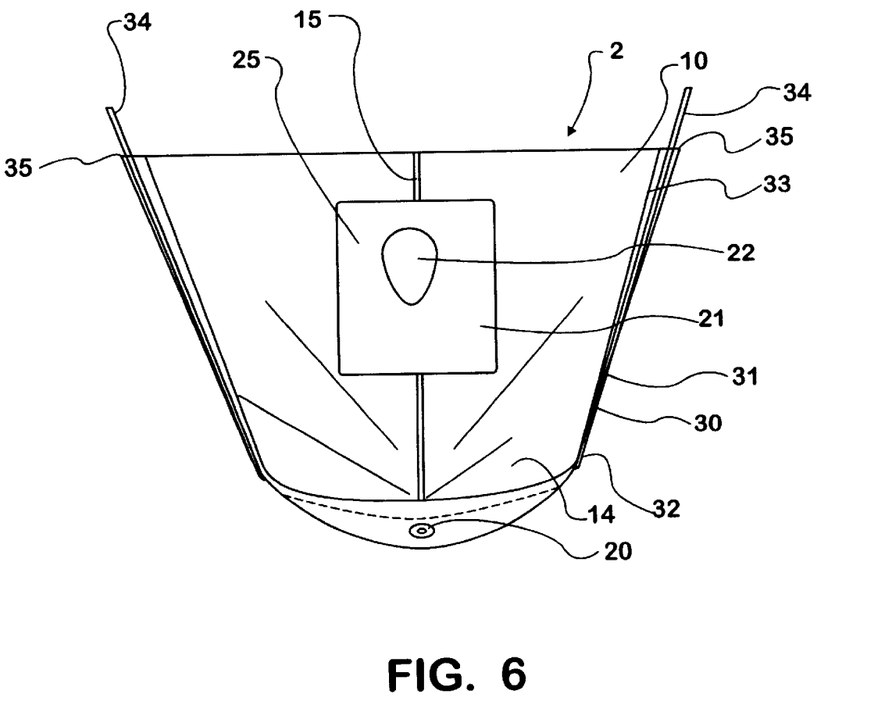
FIG. 6 is a bottom view of the shoulder pouch in open position showing the exterior of the device according to one embodiment of the invention.

In general and as shown in FIG. 1, the shoulder drape of the invention comprises a shoulder pouch assembly, both the drape portion 120 and pouch 2 being adapted for placement and positioning over either the right or left shoulder of a patient. Now referring to FIGS. 1 through 9, the shoulder pouch 2 of the invention comprises a single folded sheet 10 of flexible fluid impermeable material having a front distal portion 11 and a rear proximal portion 12 relative to the patient's body. The shoulder pouch 2 also contains a top portion 13 and bottom portion 14. The flexible sheet 10 is composed of a single contiguous sheet having an overall conical configuration with the ends of the flexible sheet connected in a fluid-tight seal 15 along the rear portion 12.

Preferably, the bottom portion 14 of the flexible sheet 10 contains a fluid exit valve 20 positioned proximal to the end of the bottom portion 14. The fluid exit valve 20 can be adapted to be opened and closed, and functions to permit the egress of collected fluid from the pouch for disposal. The fluid exit valve 20 can further be adapted to connect to a catheter (not shown) attached thereto.

Figure 9:
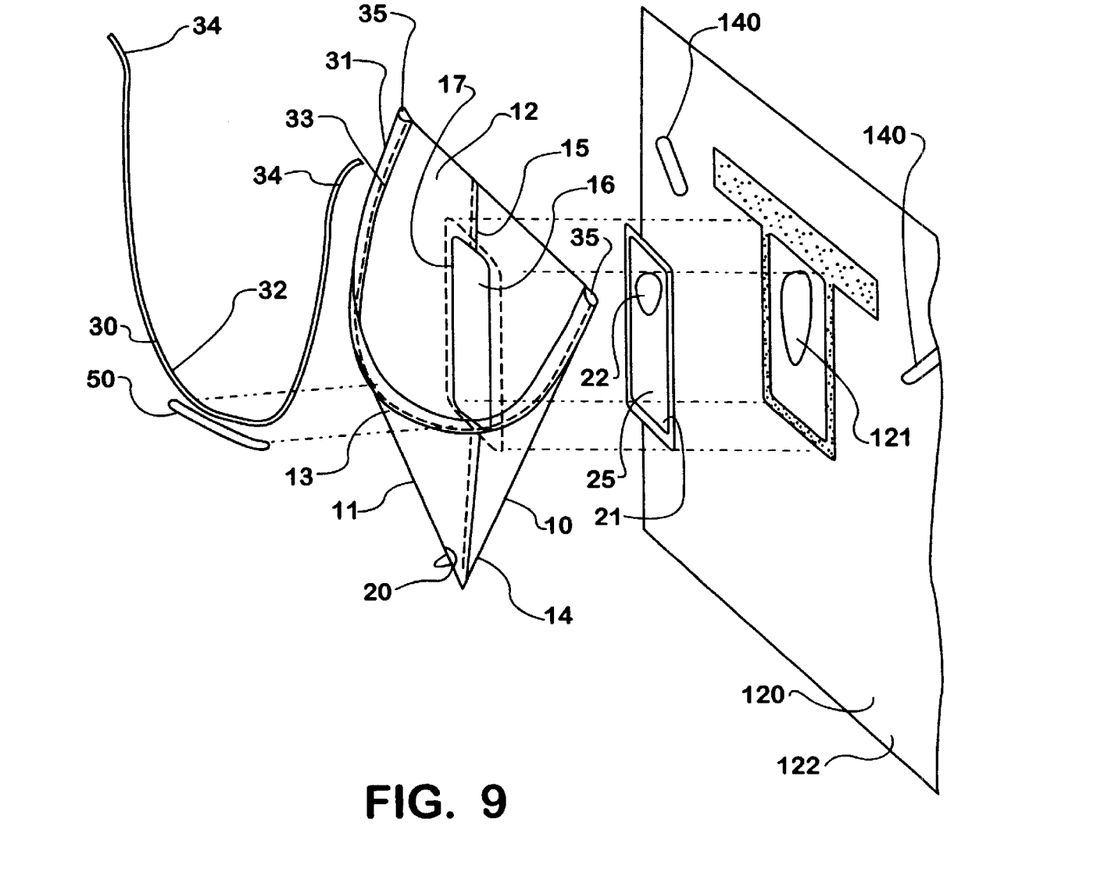
FIG. 9 is an exploded view of the individual components of a central portion of a shoulder drape containing the shoulder pouch showing the separate components in accordance with one embodiment of the invention.

The central region of the rear portion 12 of the flexible sheet 10 of the shoulder pouch 2 contains an opening 16 (see FIG. 9). The flexible sheet opening 16 is covered by an elastomeric sheet 25. The height and width of the elastomeric sheet 25 are such that the perimeter portion of the elastomeric sheet 25 extends beyond the dimensions of the opening 16 and is completely circumscribed by the flexible sheet 10. The perimeter portion 21 of the elastomeric sheet 25 is affixed to the perimeter portion 17 of the flexible sheet surrounding the opening 16.

The elastomeric sheet 25 contains a contoured opening 22 smaller in size than the opening 16 of the flexible sheet 10 and adapted to accommodate the insertion of the patient's arm 100 (see FIG. 1) when inserted therethrough. The contoured opening 22 is also adapted to accommodate the natural geometry of the shoulder anatomy and create a circumferential seal which completely surrounds the patient's shoulder 101. In a preferred embodiment, the contoured opening 22 is pear-shaped (as illustrated). Various overall opening sizes, e.g., pear-shaped openings, can be used in accordance with the invention for the particular dimensions of the patient's shoulder.

The top portion 13 of the pouch 2 contains a longitudinal wire 30 running along the upper edge 31 of the front portion 11 of the pouch 2. The middle portion 32 of the wire 30 is contained within the upper edge 31. The middle portion 32 of the wire 30 can be contained within the upper edge 31 by different means provided longitudinal movement of the wire 30 within the upper edge 31 is permitted. Preferably, the middle portion 32 of the wire 30 is contained within a seam 33 running along the top 13 of the front portion 11 of the pouch 2. Each end 34 of the wire extends beyond the ends 35 of the upper edge 31 and seam 33 of the front portion 11 near the rear portion 12. One advantageous structural feature of the invention is that the ends 34 of the wire 30 function to permit fastening of the exposed portion of the wire on the patient to secure the pouch. As a result, the width of the front portion 11 of the pouch 2 can be adjusted according to the practitioner's preference and patient's body. A malleable metallic wire is the preferred material for the wire so as to permit adjusting, shaping or contouring of the top portion of the pouch and maintaining such position. Longitudinal adjustment of the wire adjusts the size of the pouch as well.

The front portion 11 of the pouch 2 further comprises a conformable strip 50 positioned at the central region of the front portion 11 adjacent and parallel to the upper edge 31. Although preferably located in the central region of the front portion of the pouch, positions at any location along the front portion of the pouch would be expected to perform substantially the same function. In general, the conformable strip can be an elongated, flattened piece of material which can be adjusted, shaped or contoured and maintain such position. The conformable strip can be composed of any semi-rigid malleable material which can be manipulated by hand. Suitable malleable materials include, but not limited to, plastics and metals. The length of the conformable strip can vary. The wire 30 and conformable strip 50 individually and collectively function to permit precise shaping or contouring of the front portion 11 of the pouch 2 in accordance with the practitioner's preference. In further embodiment, a total of two or more individual conformable strips can be used within a single pouch.

The conformable strip is an important aspect of the invention, since it affords the user control over the conformation of the pouch portion which the longitudinal wire alone is insufficient to accomplish. In particular, the user can "arc" the conformable strip such that the general configuration of the pouch opens into a "cup" shape. The maintenance of such a configuration reduces the likelihood of the pouch collapsing or otherwise deforming during the procedure thereby reducing physical interference of the pouch with the performance of the procedure.

Although referred to as a "strip", the term is not intended to imply a limitation as to overall shape or configuration. The overall shape of the conformable strip can be in a variety of shapes and sizes provided the function of permitting conformablity of the pouch is present. The conformable strip can be, for example, rectangular, square, T-shaped, H-shaped, and the like. In a further embodiment, more than The rear portion 12 of the pouch 2 is affixed, bonded or otherwise adhered to the exterior side 122 (relative to the patient) of a surgical drape 120 as shown in FIGS. 1, 7, 8 and 9. The drape 120 contains an opening 121 (see FIG. 9) which aligns with the opening 22 of the elastomeric sheet 25. Likewise, the opening 121 of the drape 120 simultaneously aligns with the central opening 16 of the rear portion 12 of the flexible sheet 10.

In a preferred embodiment, the patient-contacting side 123 (see FIG. 8) of the drape 120 further comprises an adhesive portion 80 adapted to adhere the drape 120 (and pouch) onto the patient's body. The adhesive used in the adhesive portion 80 can be a adhesive suitable for prolonged contact with the patient's skin for the duration of the procedure.

Figure 7:
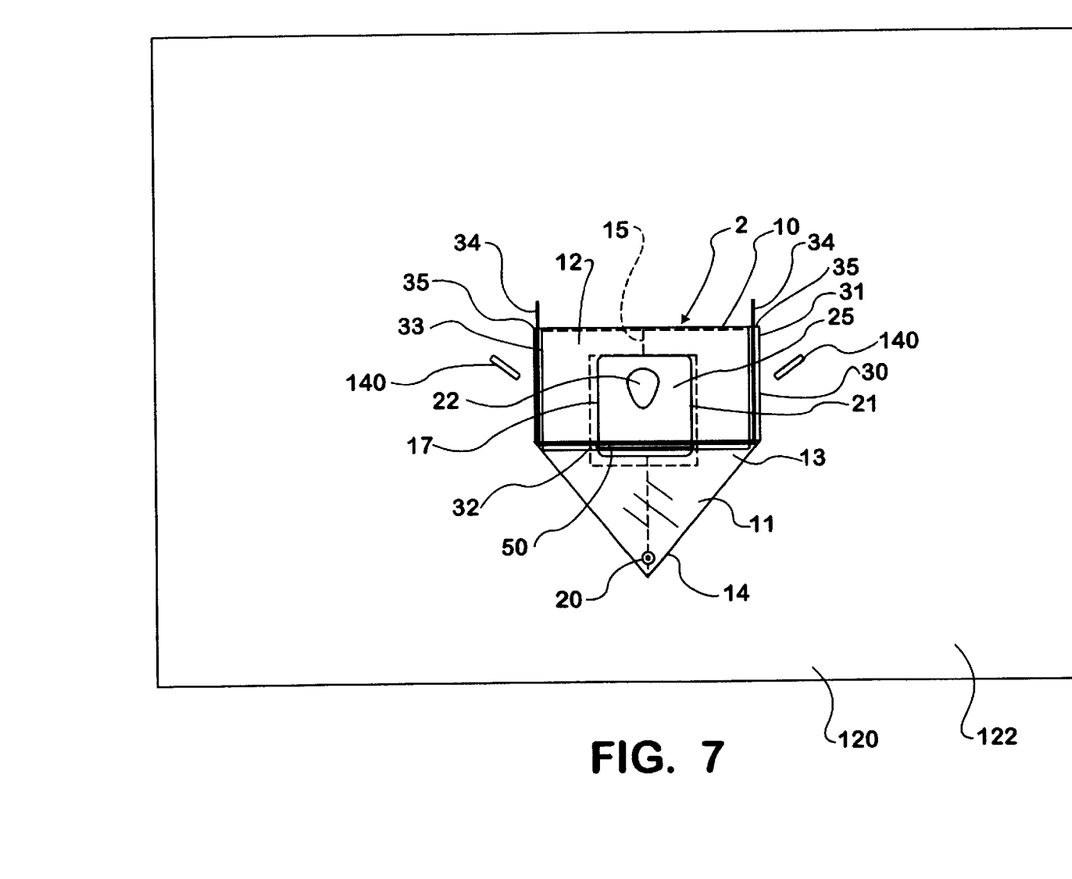
FIG. 7 is a front view of the shoulder pouch in flattened position affixed to a drape in accordance with one embodiment of the invention.
Figure 8:
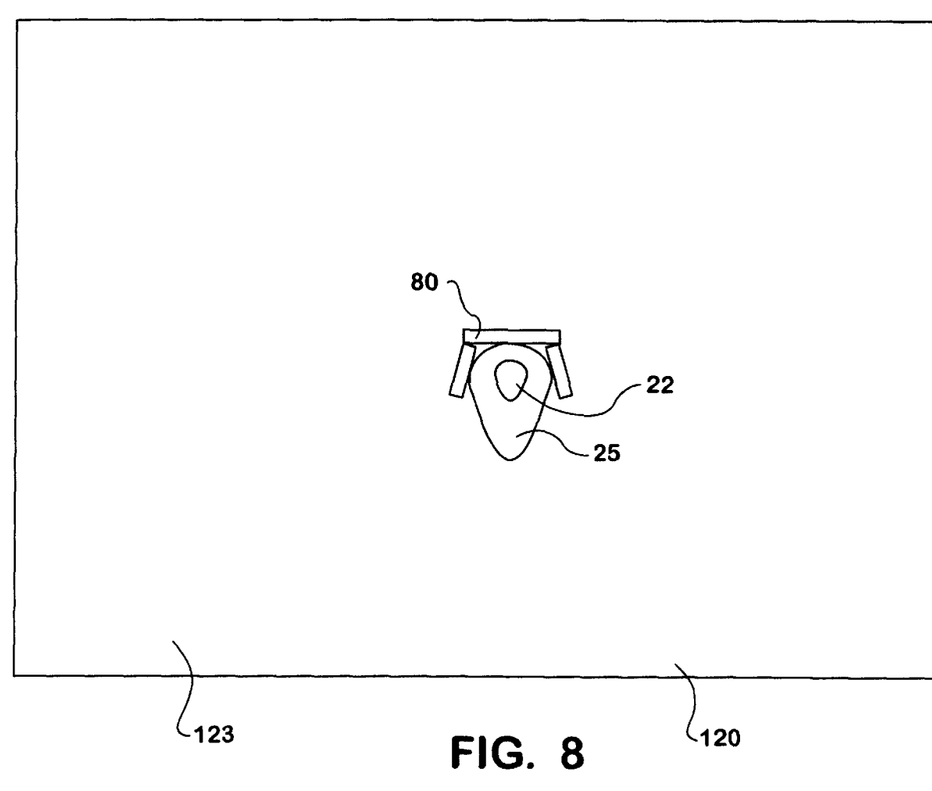
FIG. 8 is a rear view of a shoulder drape comprising the shoulder pouch affixed thereto in accordance with one embodiment of the invention.

In a further embodiment, the exterior side 122 of the drape 120 can contain additional devices affixed thereto which facilitate the surgical procedure. For example, the drape can comprise fastening means for securing the position of catheters, tubing, monitor wires, and the like. In the case of fastening means, any suitable material, device or assembly which can function to reversibly or irreversibly secure additional equipment and the like which can be affixed to the drape surface can be used. Suitable fastening means can include adhesive strips, clamps, clasps, and Velcro™ strips. In one example and as depicted in FIGS. 1, 7 and 9, a pair of Velcro™ strips 140 are shown in FIGS. 1, 7 and 9 attached to the drape 120 on each side adjacent to the pouch 2 in order to secure catheters or tubing to facilitate their control during a procedure.

The materials used for the flexible sheet of the pouch, the elastomeric sheet, surgical drape portions, as well as the adhesives, are conventional materials readily available in the art. The flexible sheet of the pouch can be composed of any fluid impervious material suitable for surgical applications. Preferably, the flexible sheet is composed of a transparent material. Examples of suitable materials for use in the flexible sheet include, but are not limited to, polymeric films such as polyethylene, polypropylene, polyester, polyvinylchloride, and combinations thereof.

The elastomeric sheet can be composed of any material having elastomeric properties which is suitable for surgical applications. Examples of such elastomeric materials include, but are not limited to, natural or synthetic rubbers.

The drape used with the pouch of the invention can be composed of any one of a variety of suitable medical fabric materials readily available in the surgical field. Such medical fabric materials can include, but are not limited to, multilaminate materials comprising a non-woven layer and a fluid impervious layer.

The flexible sheet, elastomeric sheet and drape are affixed to one another using suitable bonding techniques and materials readily available in the art. Such bonding techniques include, but are not limited to, heat sealing, ultrasonic sealing, and chemical adhesives. Double-sided adhesives can be used in accordance with the invention. Adhesives when used must be compatible with the materials and substances with which they are used. For example, an adhesive used to bond the flexible sheet to the elastomeric sheet must be chemically compatible with both materials. Likewise, an adhesive used at the patient-contacting side of the drape should be suitable for prolonged contact with the patient's skin during the procedure.

The general procedure for using the pouch and drape of the invention according to one embodiment of the invention is as follows. To place the pouch and drape onto a patient in preparation for surgery, the patient is positioned into the "beach chair" or Fowler's position. The drape and pouch are unpackaged and unfolded and the adhesive surface of the adhesive portion 80 on the patient contacting side 123 of the drape 120 is exposed. The patient's arm 100 is pulled through the opening 22 of the elastomeric sheet 25 of the pouch 2 and the elastomeric sheet 25 is pulled up and over the patient's shoulder 101 forming a seal circumscribing the perimeter of the area above shoulder. At this point, the portion of the drape 120 containing the pouch 2 can be released and unfolded. Once the rear portion 12 of the pouch 2 and drape are positioned over the shoulder 101, the adhesive portion 80 is secured into the base of the patient's neck and front of the chest and back of the shoulder. The configuration of the adhesive portion 80 can vary according to the patient's anatomy. The ends 34 of the wire 30 can then be tied together on the opposite side of the patient's neck or otherwise secured as needed. Once positioned and secure, the remainder of the drape above the shoulder is unfolded up and over the patient's head. The portion of the drape near the feet is unfolded and then toward the back to create the anesthesia screen. The pouch 2 is extended or opened and adjusted to the desired position and configuration by adjusting and shaping the wire 30 and conformable strip 50.

Industrial Applicability:

The shoulder drape of the invention provides a drape and pouch assembly containing structural features which specifically accommodate the natural geometry of the shoulder and which permit adjustment and maintenance of the configuration of the pouch as desired. Accordingly, the pouch of the invention affords the practitioner increased control over the drape and pouch throughout the procedure. In addition to creating the sterile field required for surgery, the simplicity of the design and materials permits cost-effective manufacturing.

The invention has been described with reference to various specific and preferred materials, embodiments and techniques. It should be understood by one of ordinary skill that reasonable modifications and variations of such materials, embodiments and techniques are possible without while remaining within the spirit and scope of the invention.

What we claim is:

1. A surgical shoulder pouch for use with a surgical drape comprising:

a) a single folded sheet of flexible fluid impermeable material having a front distal portion and a rear proximal portion relative to the patient's body, and top portion and bottom portion;

b) a central region located on said rear portion of the flexible sheet having an opening;

c) an elastomeric sheet covering said opening in the flexible sheet, the elastomeric sheet having a contoured opening therethrough smaller in size than the opening in the flexible sheet, said contoured opening being pear-shaped and contiguously surrounded by the elastomeric sheet material with the narrower end of the opening oriented toward the bottom of the pouch, the perimeter portion of said elastomeric sheet being fixed to the perimeter portion of the opening of the flexible sheet so that the flexible sheet circumscribes the perimeter of the elastomeric sheet;

d) a longitudinal wire having a middle portion inside of a seam running along the upper edge of the top portion of the front portion of the pouch, and having ends exiting the front portion of the pouch proximal to the rear portion of the pouch; and e) a conformable strip positioned in the front portion of the pouch adjacent and generally parallel to the upper edge.

2. The surgical shoulder pouch of claim 1 wherein said conformable strip is composed of a malleable plastic or metal.

3. The surgical shoulder pouch of claim 2 wherein said conformable strip is composed of metal.

4. A surgical drape having affixed thereto a surgical shoulder pouch comprising:

a) a single folded sheet of flexible fluid impermeable material having a front distal portion and a rear proximal portion relative to the patient's body, and top portion and bottom portion;

b) a central region located on said rear portion of the flexible sheet having an opening;

c) an elastomeric sheet covering said opening in the flexible sheet, the elastomeric sheet having a contoured opening therethrough smaller in size than the opening in the flexible sheet, said contoured opening being pear-shaped and contiguously surrounded by the elastomeric sheet material with the narrower end of the opening being oriented toward the bottom of the pouch, the perimeter portion of said elastomeric sheet being fixed to the perimeter portion of the opening of the flexible sheet so that the flexible sheet circumscribes the perimeter of the elastomeric sheet;

d) a longitudinal wire having a middle portion inside of a seam running along the upper edge of the top portion of the front portion of the pouch, and having ends exiting the front portion of the pouch proximal to the rear portion of the pouch, said wire being adapted to permit securing of the pouch onto the patient;

e) a conformable strip positioned in the front portion of the pouch adjacent and generally parallel to the upper edge;

wherein the exterior of the rear portion of said pouch is affixed to a surgical drape having an opening in alignment with said opening in the elastomeric sheet of the pouch.

5. The surgical drape of claim 4 wherein the patient-contacting surface of the drape comprises an adhesive portion adapted to adhere the drape onto the patient's body.

* * * * *